United States Patent
Laghi et al.

(10) Patent No.: US 9,937,065 B2
(45) Date of Patent: *Apr. 10, 2018

(54) METHOD AND APPARATUS OF A LINER INTERFACE WITH NEURAL RECEPTORS

(71) Applicant: The Ohio Willow Wood Company, Mount Sterling, OH (US)

(72) Inventors: Aldo A. Laghi, St. Petersburg, FL (US); Kevin McLoone, Dunedin, FL (US)

(73) Assignee: THE OHIO WILLOW WOOD COMPANY, Mt. Sterling, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/600,197

(22) Filed: Jan. 20, 2015

(65) Prior Publication Data

US 2016/0158034 A1    Jun. 9, 2016

Related U.S. Application Data

(63) Continuation of application No. 13/687,229, filed on Nov. 28, 2012, now Pat. No. 8,979,944.

(51) Int. Cl.
   *A61F 2/78* (2006.01)
   *A61F 2/72* (2006.01)
   (Continued)

(52) U.S. Cl.
   CPC ............. *A61F 2/7812* (2013.01); *A61B 5/04* (2013.01); *A61B 5/04001* (2013.01); *A61F 2/72* (2013.01);
   (Continued)

(58) Field of Classification Search
   CPC .. A61F 2/70; A61F 2/72; A61F 2/7812; A61F 2002/5064; A61B 5/6811; A61B 5/6824; A61B 5/6828
   See application file for complete search history.

(56) References Cited

U.S. PATENT DOCUMENTS

| 5,213,715 A | 5/1993 | Patterson et al. |
| 5,258,037 A | 11/1993 | Caspers .......................... 623/36 |

(Continued)

FOREIGN PATENT DOCUMENTS

| DE | 102007035409 A1 | 1/2009 |
| EP | 2737878 A1 | 4/2014 |

OTHER PUBLICATIONS

European Search Report Application No. 13 19 4821 (attached).
(Continued)

*Primary Examiner* — Thomas J Sweet
*Assistant Examiner* — Christie Bahena
(74) *Attorney, Agent, or Firm* — Benesch Friedlander Coplan & Aronoff, LLP; Benjamen E. Kern; Stephen D. Scanlon

(57) ABSTRACT

A liner interface and method of making the liner interface comprising attaching non-compressible deformable electrically conductive receptors to an inner surface of a fabric layer, placing the fabric layer into a female part of a molding machine, axially deforming the deformable receptors from their initial thickness with a male part of the molding machine, injecting a molten gel elastomer into the molding machine to completely surround and adhere to the receptors and inner surface of the tubular fabric layer, allowing the molten gel to cure, and removing the male part from the molding machine and allowing the axially deformed receptors to axially expand beyond the inner surface of the cured liner interface.

13 Claims, 4 Drawing Sheets

(51) Int. Cl.
  *A61B 5/04* (2006.01)
  *A61F 2/80* (2006.01)
  *H01R 43/00* (2006.01)

(52) U.S. Cl.
  CPC .............. *A61F 2/80* (2013.01); *H01R 43/00* (2013.01); *A61F 2210/0076* (2013.01); *Y10T 29/49117* (2015.01)

(56) References Cited

U.S. PATENT DOCUMENTS

| | | | |
|---|---|---|---|
| 5,376,132 A | 12/1994 | Gaspers | |
| 5,443,525 A | 8/1995 | Laghi | |
| 5,507,834 A * | 4/1996 | Laghi | A61F 2/80 623/34 |
| 5,676,132 A | 10/1997 | Tillotson et al. | |
| 5,785,040 A | 7/1998 | Axelgaard | 600/391 |
| 6,852,269 B2 | 2/2005 | Eberle et al. | |
| 7,377,944 B2 * | 5/2008 | Janusson | A61B 5/103 623/36 |
| 8,024,023 B2 | 9/2011 | Tolvanen | |
| 8,591,599 B1 | 11/2013 | Kaliki et al. | 623/25 |
| 2005/0101693 A1 | 5/2005 | Arbogast et al. | 523/122 |
| 2007/0021841 A1* | 1/2007 | Al-Temen | A61F 2/54 623/25 |
| 2009/0132056 A1 | 5/2009 | Kania | |
| 2009/0216339 A1* | 8/2009 | Hanson | A61B 5/0492 623/25 |
| 2010/0004524 A1 | 1/2010 | Yuen | |
| 2010/0114238 A1 | 5/2010 | Muccio | |
| 2010/0318195 A1 | 12/2010 | Kettwig et al. | |
| 2011/0270414 A1* | 11/2011 | Laghi | A61F 2/7812 623/36 |
| 2012/0190989 A1 | 7/2012 | Kaiser et al. | |
| 2012/0253475 A1 | 10/2012 | Kelley | |
| 2012/0296445 A1 | 11/2012 | Leiniger et al. | 623/25 |
| 2013/0046392 A1 | 2/2013 | Venu et al. | 623/23.53 |
| 2013/0331950 A1 | 12/2013 | Laghi et al. | 623/36 |

OTHER PUBLICATIONS

Daly. Clinical Application of Roll-on Sleeves for Myoelectrically Controlled Transradial and Transhumeral Prostheses. Journal of Prosthetics and Orthotics. vol. 12, No. 3. pp. 88-91.
ABB. Silicone Rubber Product Information. May 15, 2005.
Dupont Tyvek Products. Verified by the Wayback Machine Aug. 6, 2012.
Ossur (pp. 1 and 2) (Iceross Original Locking Liner) Verified by the Wayback Machine Dec. 21, 2010.

* cited by examiner

Prior Art

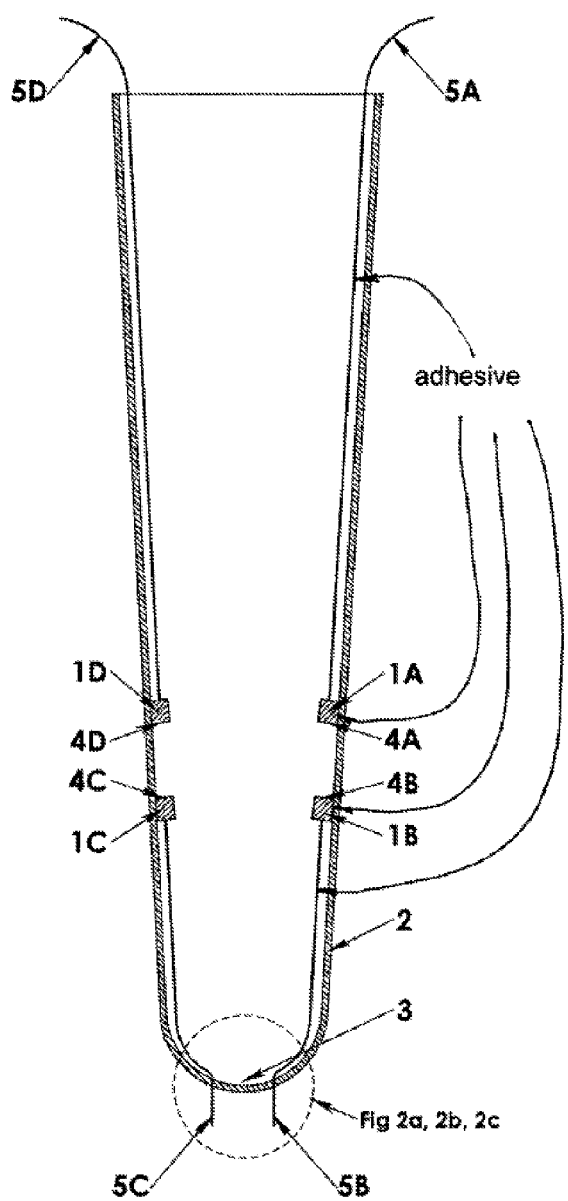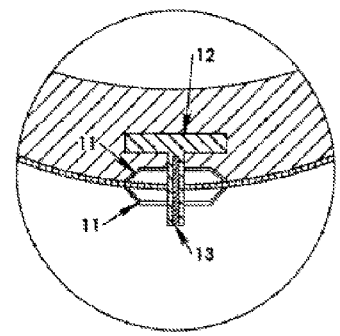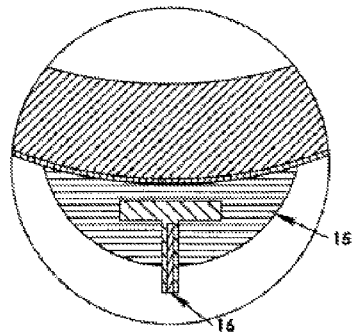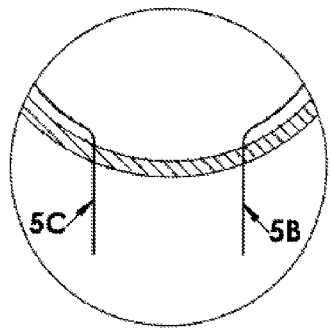

METHOD AND APPARATUS OF A LINER INTERFACE WITH NEURAL RECEPTORS

CROSS-REFERENCE TO RELATED APPLICATIONS

This application claims priority to U.S. patent application Ser. No. 13/687,229 filed on Nov. 28, 2012, the contents of which are incorporated by reference herein in their entirety.

THE NAMES OF THE PARTIES TO A JOINT RESEARCH AGREEMENT

This application is a result of activities undertaken within the scope of a joint research agreement between Alps South, LLC and the Rehabilitation Institute of Chicago that was in effect on or before the date of the research leading to this application was made.

BACKGROUND OF THE INVENTION

The present invention relates generally to a gel cushioned interface and a method of making a gel cushioned interface made of polymer material with heat resistant and electrically conductive neural receptors housed strategically within and potentially raised slightly above the inner surface of the polymer material to be worn over a limb or body surface for the purpose of conducting and/or receiving impulses through the interface.

The use of myoelectrics in the orthotics and prosthetics field started with the basic use of a conductive metal dome placed on a user's particular muscle group to pick up neural signals from nerve endings through the skin. With such a system, when the user would fire the bicep muscle, for example, the dome would pick up the signal and send it to the powered prosthesis telling it to create flexion in the prosthetic elbow. Many metal domes would be affixed to the skin of the end user externally and hard-wired (sometimes long distances) into the powered prosthetic device so that the user could fire off certain muscle groups to control functionality of the prosthesis.

More recent improvements to myoelectrics in the field involve using a series of metal domes that are punctured through and embedded in an otherwise traditional liner interface after the molding process, that are then connected to a CPU using external wires that control the powered prosthesis. Concurrently, other developments are taking place where metal electrodes are actually implanted into the user's pectoral muscle and hardwired to a CPU for cognitive control over the prosthesis.

The process of surgically inserting metal domes into a user is obviously a very invasive procedure that many potential users are unwilling to undergo. The post-molding process of puncturing holes into a liner to insert metal domes is also a difficult process that is time consuming and jeopardizes the original liner's structural integrity and durability. Thus, the need in the market exists for an interface liner that contains electrically conductive receptors that can make the appropriate amount of skin contact necessary to reliably pick up electrical impulses from very specific points on the user while also containing a means of transferring these impulses to a central processing unit.

One attempt that has been made to satisfy this need is disclosed in USPGPUB 20090216339 A1 to Hanson, et al., incorporated herein by reference. As best illustrated in FIG. 1 (10) or FIG. 2 (20), Hanson suggests affixing "domes" made of conductive silicone onto existing prosthetic liners after the molding process has taken place. Hanson focuses on the silicone dome's ability to create total contact on the skin surface, while also being properly affixed to the liner with an appropriate adhesive such as RTV silicone for silicone liners or moisture-activated urethane for urethane liners to form a more secure "butt joint" to hold the domes securely in place once they are added to the liner. USPGPUB 20100114238 A1 to Muccio incorporated herein by reference discloses a prosthetic liner, as best illustrated in FIGS. 1 and 2, having stimulation electrodes made of conductive hydrogel 105 integrated into the liner material during the molding process that are designed to be flush with the skin 106 on the inside of the liner and connected to a CPU by silver fabric conductors 103. USPGPUB 2010/0318195 A1 to Kettwig, et al. incorporated herein by reference discloses an orthopedic interface having electrically conductive coatings 23 on the inner fabric surface of the liner.

While these ideas seek to address the need for improving end user comfort while not jeopardizing functionality, they fail to address the need for a single off the shelf product that combines the manufacturability of having the electrodes molded into the inner material during a "one shot" manufacturing process while still allowing those same domes to provide an adequate amount of compression on the localized skin necessary to get a consistent myoelectric signal.

BRIEF SUMMARY OF THE INVENTION

The invention is made up of a gel cushioned liner with soft (10-40 durometer on type "A" scale) heat resistant silicone patches made of electrically conductive non-compressible deformable silicone material or electrically non-conductive non-compressible deformable material covered in any number of conductive metals or materials (copper, silver, carbon, conductive fabric, etc.) molded into the interface liner during the manufacturing molding process. The terminology "axial deformation" herein is used to describe the reduction or expansion in thickness of the silicone patches. The manufacturing process for a preferred embodiment of the invention is carried out by a conventional molding machine as, for example, illustrated in FIG. 1. During a molding process by the molding machine (10), the male core part (6) will be spaced from the female part (8) by a predetermined distance defining a predetermined annular space. A gel liner that serves as an ideal liner interface for housing the electrically conducive silicone components, while at the same time being as comfortable and minimally invasive as possible to the end user is the ALPS Gel Liner. During use of the liner, these patches are pressed against the skin of the end user to a degree that allows them to more reliably pick up neural impulses fired by nerve endings of particular muscles to aid in controlling a powered prosthesis.

The patches have an initial predetermined thickness greater than the annular space between the male and female parts of the molding machine. The patches are attached, for example by adhesive, at selected points on an interior surface of a tubular fabric layer designed as an outer fabric layer of a finished liner interface. As illustrated in FIGS. 2-4, a preferred embodiment of the present invention, although not limited thereto, includes a tubular fabric layer (2) illustrated to have a closed distal end and an open proximal end for a BK or AK liner. However, as stated above, the drawings are exemplary of a preferred use for the invention. Other uses could include arm prosthetics or other liners used on other body locations where it is desirable to monitor neural impulses for powering prosthetic and/or orthotic devices or simply monitoring for diagnostic purposes. After attaching the patches, the fabric layer (2) is placed in the female part of the molding machine. The male core part is then mated with the female part wherein the patches are axially deformed a slight distance and the annular space is closed. Next, a molten gel material (silicone, other TPE elastomers, copolymer Styrenic gels, polyurethane gel, etc.) is injected into the annular space to completely fill the annular space thereby adhering to the tubular fabric layer and around the patches, while leaving their surface area against the male part free of any molten material. When the liner is cured and removed from the molding machine, the patches are free to axially deform by expanding slightly from 0.0" to 0.25" beyond the inner surface of the cured gel layer and thereby toward the skin of the end user when in use so that the patches can have direct contact with the subcutaneous tissue superficial to the nerve that is strong enough to ensure a solid and consistent signal at all times, while still being soft enough to promote end user comfort.

The neural impulses can then be linked back through the conductive patches and into a CPU of the prosthetic via a network made up of any number of flexible materials exhibiting very low levels of resistivity (carbon filament, copper filament, silver thread, carbon fabric, copper fabric, silver fabric, traditional light gauge wire, etc.) that are also integrated into the inner gel portion of the liner interface as discussed hereinafter.

BRIEF DESCRIPTIONS OF THE SEVERAL VIEWS OF THE DRAWING(S)

FIG. 2 is a sectional view of the liner interface of a preferred embodiment of the present invention with the silicone patches adhered to the inside surface of the outer tubular fabric layer of the liner interface before the injection molding process.

FIG. 2a and FIG. 2b are enlarged sectional views of alternative distal encapsulations (3) circled in FIG. 2 that could be attached to the distal end of a preferred embodiment of the present invention.

FIG. 2c is an enlarged sectional view of an alternative distal end of the cushioned interface of FIG. 2 that could be used as an alternative to the distal encapsulations in FIGS. 2a and 2b.

Figure 1:
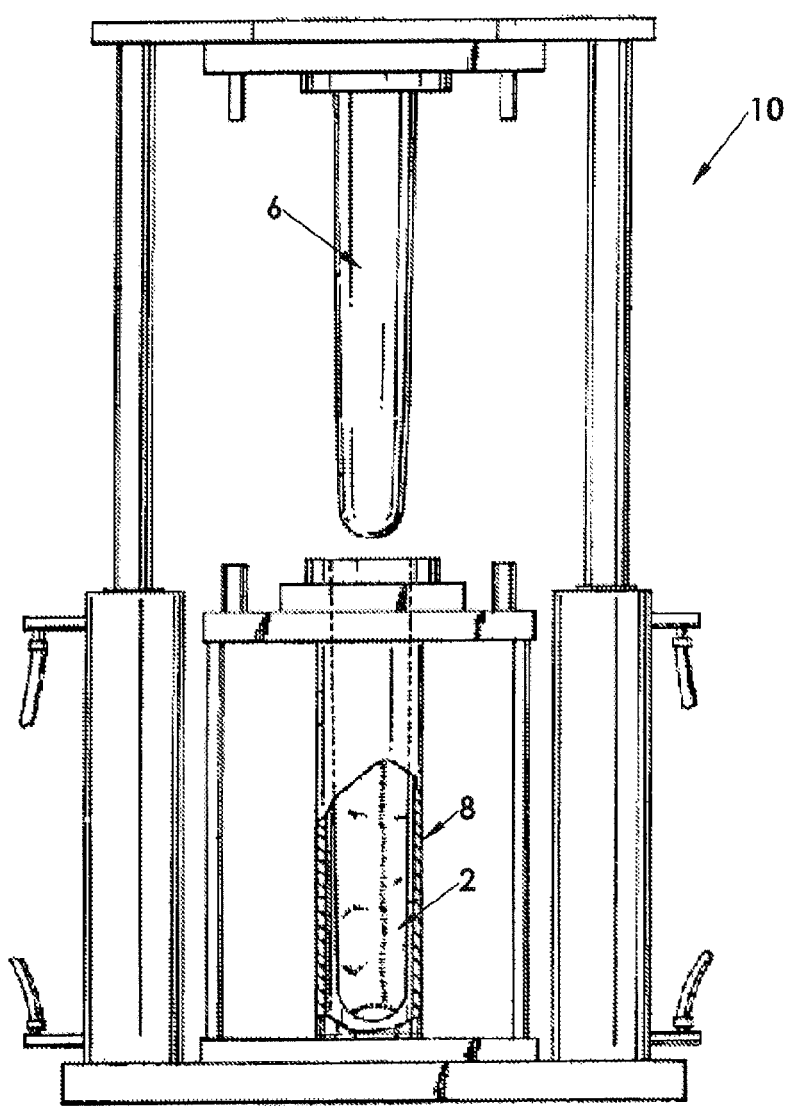
FIG. 1 shows a conventional molding machine of the same design that can be used to manufacture a prosthetic liner interface, which is a preferred embodiment of the present invention.
Figure 3:
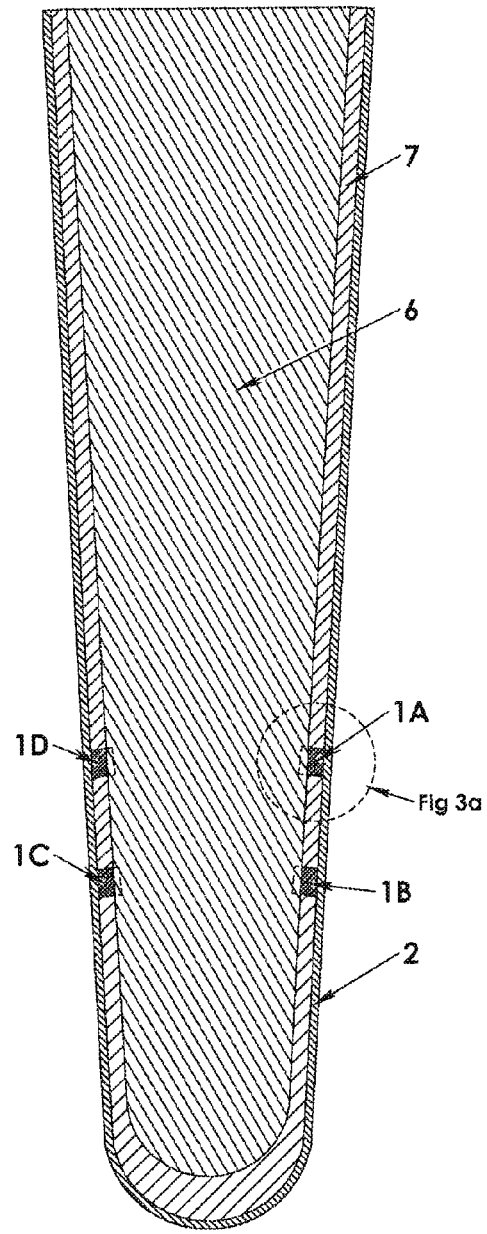

FIG. 3 is a sectional view of the liner interface of a preferred embodiment of the present invention once the tubular fabric layer has been placed inside the female portion of the molding machine and the male core portion of the molding machine has been inserted into the inside of the tubular fabric layer with the receptor patches compressed inside the mold as the core portion fills out the inside of the cavity.

Figure 3A:
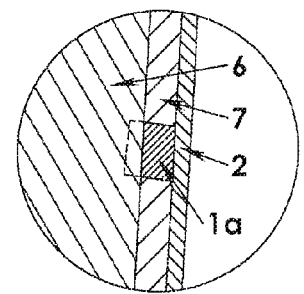

FIG. 3a is an enlarged sectional view of one of the receptors in FIG. 3 being compressed to some degree (shown in dashed lines) by the core prior to the molding process.

Figure 3B:
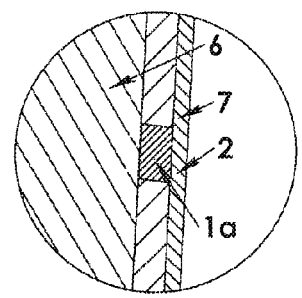

FIG. 3b is an enlarged view of another receptor in FIG. 3 that could alternatively be compressed very little or none at all to remain "flush" with the core during molding.

Figure 4:
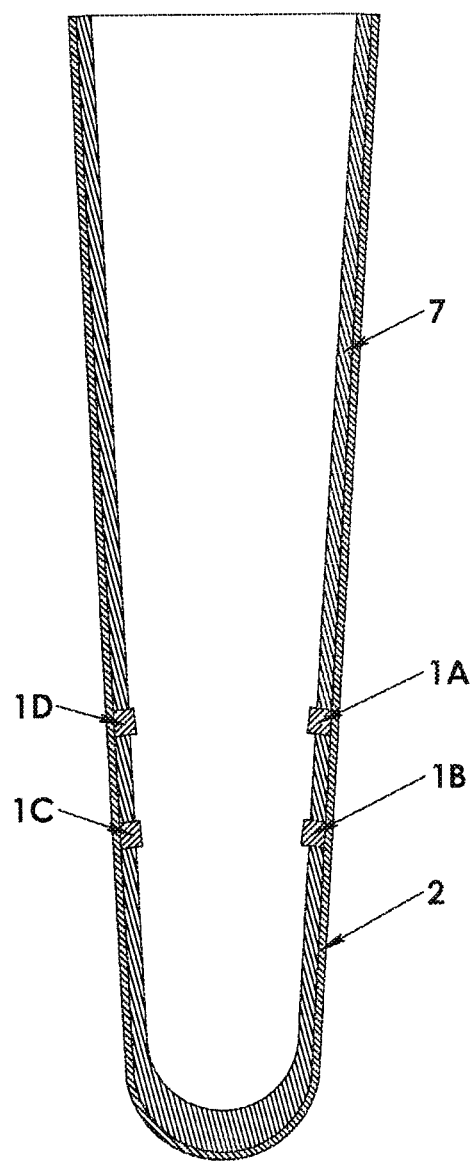

FIG. 4 is a sectional view of the liner interface of a preferred embodiment of the present invention that shows the once compressed patches returning to their full uncompressed shape after the injection molding process is completed.

DETAILED DESCRIPTION OF THE INVENTION

The present invention as illustrated in FIG. 2, includes a sewn fabric tubular layer (2) having longitudinal stretch characteristics of 5% to 180%, transverse stretch characteristics of 10% to 250%, and fabric thickness of 0.30 mm to 1.5 mm. As indicated by circle (3), a distal attachment may be attached to the distal end of the fabric tubular layer (2). As shown in FIG. 2a and FIG. 2b, a first distal attachment includes grommets (11) and an umbrella (12, 15) assembly crimped to the closed end that is then encapsulated during the molding process. The umbrella (12, 15) assembly includes an outwardly extending threaded bore (13, 16) for receiving a threaded pin as part of a locking assembly. As shown in FIG. 2b, a distal attachment is attached to the outer surface of the distal end of the fabric layer subsequent to the molding process and encapsulated thereto using a Liquid Silicone Rubber of approximately 60 durometer silicone to complete the distal attachment (3). While the liner illustrated includes the various distal attachments (3), exemplified in more detail in FIGS. 2a and 2b, it is important to note that the liner could alternatively be of the cushioned variety as in FIG. 2c, i.e., an interface without a distal attachment but reinforced with a distal cushioning element.

Referring to FIG. 2, the preferred receptor patches (1A-1D) are preferably made of non-compressible deformable Heat Resistant Silicone such as CLS 60-10 or any other low durometer silicone that is heat resistant and of a silicone that is either electrically conductive silicone, or non-electrically conductive silicone but individually wrapped with an electrically conductive medium (4A-4D) using any number of common adhesives such as traditional glue, bonding fabrics, fusible fabrics, or silicone based adhesives. Such electric conductive medium may preferably consist of Silver Fabric (or any other fabric or otherwise unobtrusive medium with low resistivity, including copper or carbon fabrics and/or light gauge wire), that covers each patch completely and includes strips (5A-5D) extending from each patch to encompass the length of the liner as a whole. The ends of these strips (5A-5D) can then be passed through the distal end of the liner to be connected to a CPU. Conversely, the conductive strips can also be fed out the proximal end of the liner, both the distal and proximal ends of the liner, or any other advantageous point throughout the liner to be affixed to a CPU for processing. The silicone patches and length of conductive strips are then strategically attached (glued, sewn, silicone based adhesive, etc.) to the inner surface of the fabric tubular layer prior to the placement of the fabric tubular layer into the female part of the molding machine. The silicone patches and strips are placed in specific predetermined areas targeting specific nerve endings.

The preferred shape of the silicone patches is disc-shaped so that they can be tapered flush with the gel with the dome area extending slightly above to improve contact on the nerve endings. However, other shapes can equally be employed, such as square-shaped, rectangle-shaped, diamond-shaped, oval-shaped or any other configuration necessary to accommodate the particular area to be sensed. Furthermore, the four patches illustrated in the figures is not intended to limit the number of patches that can be provided on any single liner which would depend of the type of prosthetic, orthotic or diagnostic equipment to be controlled.

Also, the silicone discs are used for their properties highlighted above, but other heat resistant and deformable space fillers could potentially be wrapped in silver fabric (or substitute) and adhered to the fabric in a similar fashion such as heat resistant rubbers, etc.

As illustrated in FIG. 3, the male mold (6) is then lowered down into the center of the opened fabric tubular layer (2). The silicone discs (1A-1D) are now axially deformed a predetermined amount (preferably approximately 0.01"-0.25") by the male mold as denoted by the phantom lines in FIG. 3 and FIG. 3a. Alternatively, the discs (1A-1D) could be flush with the surface of the male mold (6) as demonstrated in FIG. 3b. Any combination of these options exist for any number of receptors. The amount of initial axial deformation (reduction in thickness) of the silicone discs would be predetermined by the amount of axial deformation (axial expansion) desired of the discs during the post molding process. It is noted that the molding procedure itself with the exception of the discs and strips is identical to the molding process of a traditional ALPS Locking Liner.

The Liner is then injection molded with the hot (300-400 degrees Fahrenheit) molten gel elastomer (7) exhibiting stretch characteristics of 600%-2,000% and a Modulus of 50-500 psi when cured. Such gel elastomers include silicone, thermoplastic elastomers [triblock], copolymer Styrenic gels, and polyurethane gels, etc. The preferred gel elastomer (7) is the ALPS elastomer but any of the above elastomers could be used in their molten stage to fill the annular space in the molding machine and completely engulf the silicone discs with the exception of the interface between the discs and male core part, and the strips thereby adhering to the inner surface of the tubular fabric layer, the discs and strips. Thus, the discs and the conductive strips are locked in place to ensure durability and an exact location.

As illustrated in FIG. 4, once the molding process is completed and the male portion of the mold is removed, the axially deformed silicone discs (1A-1D) will be free to axially expand. Due to the adhesion of the injected gel to the sides of the discs, the discs will not expand back to their initial thickness, but will expand back to an extent past the inner surface of the cured liner depending on the initial axial deformation of the discs during the molding process to thereby improve pressurized contact on the nerve endings while still being completely integrated into the inner liner material. The amount of axial expansion of the discs subsequent to the curing steps will depend on the amount of axial deformation exerted on the initial thickness of the discs during the molding process. The cured gel around the discs will thereby stabilize the receptor to the nerve ending when in use.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, all publications and patent documents referenced herein are incorporated herein by reference in their entireties.

What is claimed is:

1. A prosthetic liner interface comprising:
a fabric layer having an inner surface and an outer surface;
a gel layer having an outer surface overlying the inner surface of the fabric layer, and having an inner surface exposed for contact with the skin of a user;
an electrically conductive neural receptor including a silicone patch reaching fully through the gel layer between the inner and outer surfaces of the gel layer, the patch having an inner surface attached directly to the fabric layer on the inner surface of the fabric layer, a side surface adhered to the gel layer fully between the inner and outer surfaces of the gel layer, and an outer surface exposed for contact with the skin of a user; and
an electrically conductive element configured to conduct electric signals caused by neural impulses from nerve endings when the exposed outer surface of the silicone patch is in direct contact with the skin of a user, the conductive element comprising a conductive strip attached to the inner surface of the fabric layer and extending from the silicone patch between the fabric layer and the gel layer.

2. The prosthetic liner interface of claim 1, wherein the fabric layer has an open proximal end and a closed distal end, the conductive strip has an end coupled with the silicone patch, and the conductive strip further has an opposite end extending outward through the closed distal end of the fabric layer.

3. The prosthetic liner interface of claim 1, wherein the silicone patch is wrapped with an electrically conductive medium.

4. The prosthetic liner interface of claim 3, wherein the conductive strip is formed as an extension of the electrically conductive medium.

5. The prosthetic liner interface of claim 3, wherein the electrically conductive medium is adhered onto the silicone patch.

6. The prosthetic liner interface of claim 1, wherein the silicone patch is disc-shaped, square-shaped, rectangular-shaped, oval-shaped or diamond-shaped.

7. The prosthetic liner interface of claim 1, wherein the gel material coating comprises silicone, thermoplastic triblock elastomers, copolymer Styrenic gel, or polyurethane gel.

8. The prosthetic liner interface of claim 7, wherein the gel material coating exhibits stretch characteristics of 600%-2000% when cured.

9. The prosthetic liner interface of claim 1, wherein the fabric layer has an open proximal end and a closed distal end, the conductive strip has an end coupled with the silicone patch, and the conductive strip further has an opposite end extending outward through the open proximal end of the fabric layer.

10. The prosthetic liner interface of claim 1, wherein the conductive element is sewn to the fabric layer.

11. The prosthetic liner interface of claim 1, wherein the conductive element comprises a filament or thread.

12. The prosthetic liner interface of claim 1, wherein the conductive element is adhered to the inner surface of the fabric layer.

13. The prosthetic liner interface of claim 1, wherein the conductive element comprises a fabric.

* * * * *